United States Patent [19]

Lew

[11] Patent Number: 4,591,268
[45] Date of Patent: May 27, 1986

[54] ACCUMULATIVE ABSORPTION-DISPERSION SPECTROPHOTOMETER

[76] Inventor: Hyok S. Lew, 7890 Oak St., Arvada, Colo. 80005

[21] Appl. No.: 674,499

[22] Filed: Nov. 23, 1984

[51] Int. Cl.$^4$ .............................................. G01N 21/00
[52] U.S. Cl. ...................................... 356/338; 356/36; 356/38; 356/246; 356/335; 250/432 R
[58] Field of Search ............ 356/36, 38, 246, 335–336, 356/338, 319, 343; 250/432 R, 433, 435

[56] References Cited

U.S. PATENT DOCUMENTS 3,306,157 2/1967 Mach .................................. 356/343
4,341,471 7/1982 Moss et al. .......................... 356/343

Primary Examiner—R. A. Rosenberger
Assistant Examiner—Crystal Cooper

[57] ABSTRACT

This invention relates to a spectrophotometer that detects the types and amounts of certain chemical elements dissolved or suspended in a liquid or gas medium. A light beam of desirable frequency emitted from a light source passes through the mass concentration boundary layer adjacent to a filter surface, which filter functions as a selective barrier selectively blocking chemical elements or impurities under detection from moving thereacross. Prior to the start of a measurement, the filter surface is washed with the sample medium to be analyzed by allowing the sample medium to flow parallel to the filter surface without flowing across the filter. The measurement starts at the moment the outlet of the washing flow is shut-off whereupon a light sensor such as photoelectric sensor records the intensity of the light beam passing through the mass configuration boundary layer. As the dissolved or suspended chemical elements accumulates in the mass concentration boundary layer adjacent to the filter, the read out by the light sensor decreases in intensity because of the light adsorption or dispersion by the chemical elements accumulating in the mass concentration boundary layer. The time rate of the decrease of the normalized light intensity measured by the light sensor depends only on the rate of the sample flow across the filter and the percent mass of the chemical elements dissolved or suspended in the medium, but it is absolutely independent of the physical or optical boundary conditions of the measuring apparatus. The normalized light intensity is the instant light intensity divided by the initial light intensity measured at the beginning of the measuring cycle immediately after the completion of the washing cycle. The normalized light intensity of the dispersed light through the mass concentration boundary layer can be used to measure the turbidity of the sample medium. When the filter is opaque, the light beam is directed substantially parallel to the surface of the filter through the mass concentration boundary layer. When the filter is light-transparent, the light beam may be directed across the filter. When the filter surface is light-reflective, the light sensor may measure the intensity of the reflected light that passes twice through the mass concentration boundary layer.

11 Claims, 14 Drawing Figures

ACCUMULATIVE ABSORPTION-DISPERSION SPECTROPHOTOMETER

BACKGROUND OF THE INVENTION

As our environment becomes more and more polluted, and ever-increasingly more powerful toxic elements are isolated and released in our environment, there has been a great demand for methods or tools which can measure very very small amounts of chemical elements dissolved or suspended in air, water, and other industrial fluid mediums. One of the major difficulties involved in the conventional spectrophotometric apparatus used to measure an extremely minute amount of chemical elements dissolved or suspended in a carrier fluid medium is to isolate the change in the light intensity that is caused by the chemical element from other changes resulting from the physical and optical boundary conditions associated with the spectrophotometric apparatus. In other words, one has to know the precise reading indicated by the apparatus when the sample is perfectly pure. Then, one can compare the reading on an impure sample with the reading on the pure sample and determine the degree of impurity. The dilemma is that the actual reading on a contaminated sample has to be always compared with an old reading on a perfectly pure sample because there is no way to measure a perfectly pure sample and a contaminated sample with the same apparatus at the same time and, consequently, there is always a doubt about the old reading on a perfectly pure sample which changes in time as the condition of the apparatus changes in time. This problem of uncertainity or of creeping error has no easy solution and is being tackled by an extremely painstaking and time-consuming process at the present time.

The primary object of the present invention is to provide a spectrophotometer or turbidity meter that measures the concentration of chemical elements or impurities accumurated in the mass boundary layer adjacent to a filter that blocks the movement of the chemical elements or impurities thereacross while allowing the flow of the carrier medium thereacross.

Another object of the present invention is to provide a spectrophotometer or turbidity meter that has a built-in reference reading that plays a role equivalent to the reading on the pure sample in the conventional spectrometer or turbidity meter.

A further object of the present invention is to provide a spectrophotometer or turbidity meter employing a single light path-single sample cell combination that replaces the dual light path or dual sample cell method employed in conventional spectrophotometric apparatus.

Yet another object of the present invention is to provide a spectrophotometric technique that measures transient mass concentration within the mass boundary layer adjacent to a filter for a finite period immediately following a washing period wherein this combination of washing-measuring cycle is repeated over and over in order to provide a continuous reading on the sample continuously passed by or through the filter.

Yet a further object of the present invention is to provide a spectrophotometer that has enough versatility to measure an extremely low level of impurity as well as a high degree of impurity, which versatility is provided by means for varying the period of each washing-measuring cycle.

Still another object of the present invention is to provide a spectrophotometer that is installed in-line and continuously monitors the medium flowing through the line without requiring frequent cleaning and calibration.

Still a further object of the present invention is to provide a spectrophotometer measuring the transient mass concentration in a mass boundary layer adjacent to an opaque filter.

Additionally another object of the present invention is to provide a spectrophotometer measuring the transient mass concentration in a mass concentration boundary layer adjacent to a light-transparent filter.

Additionally a further object of the present invention is to provide a spectrophotometer measuring the transient mass concentration in a mass concentration boundary layer adjacent to a light-reflecting filter.

These and other objects of the present invention will become clear as the description thereof proceeds.

BRIEF DESCRIPTION OF FIGURES

The present invention may be described with greater clarity and specificity by referring to the following figures.

DESCRIPTION OF THE PREFERRED EMBODIMENTS

Figure 1:
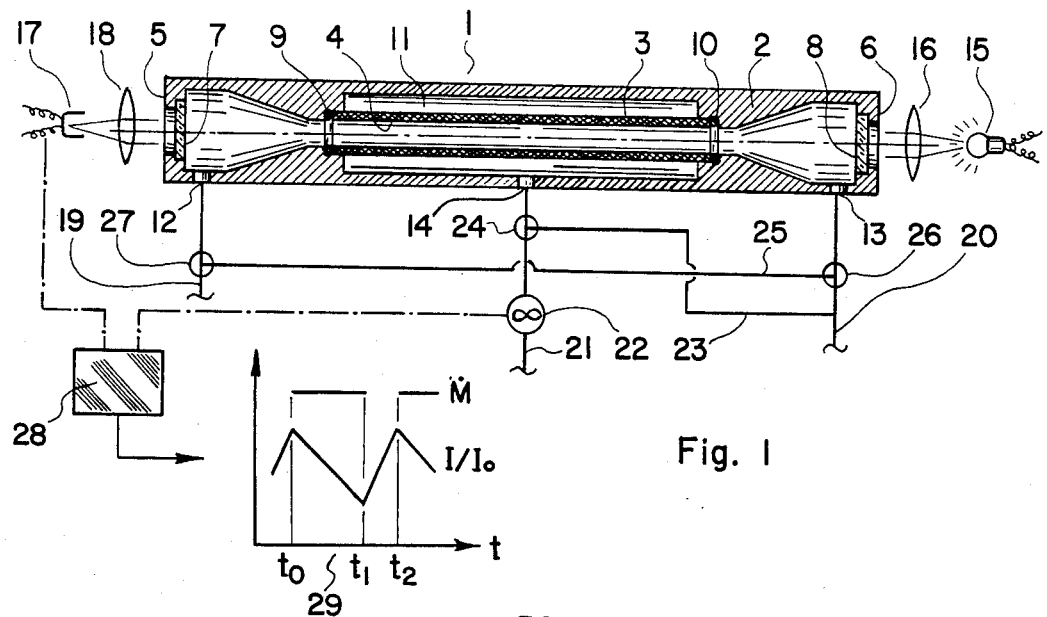
FIG. 1 illustrates a cross section of an embodiment of the accumulative absorption spectrophotometer of the present invention wherein a tubular filter of a small diameter is employed in creating a mass concentration boundary layer.

In FIG. 1 there is illustrated a cross section of an embodiment of the accumulative absorption spectrophotometer constructed in accordance with the principles of the present invention, which cross section is taken along a plane including the central axis of the apparatus. The accumulative absorption spectrophotometer 1 comprises a hollow cylindrical body 2 made of an opaque material and a tubular filter 3 of a small diameter coaxially disposed therein, which combination provides a straight through hole 4 extending from one extremity 5 to the other extremity 6 of the hollow cylindrical body 2. A pair of light-transparent windows 7 and 8 close the two extremities of the through hole 4 in a leak-proof manner. A pair of O-rings 9 and 10 provide leak-proof fittings between the hollow cylindrical body and the tubular filter 3. There is a cylindrical annular cavity 11 intermediate the tubular filter 3 and the cylindrical wall of the body 2 that surrounds the tubular filter 3. The through hole 4 includes a pair of ports 12 and 13 disposed adjacent to two windows 5 and 6, respectively. The cylindrical annular cavity 11 includes a port 14 disposed at the mid-section thereof. A light source 15 emitting a light beam of preferred frequency and a light directing means 16 such as a lens are disposed adjacent to one window 8 exteriorly in a coaxial relationship with respect to the center line of the through hole 4. A light detecting means 17 such as a photoelectric sensor and a light-focusing means 18 such as a lens are disposed adjacent to the window 7 exteriorly in a coaxial relationship with respect to the center line of the through hole 4. One of the two ports 12 and 13 open to the through hole is connected to a sample outlet tubing 19, while the other of the two ports 12 and 13 is connected to a sample inlet tubing 20. The port 14 open to the cavity 11 is connected to another sample outlet tubing 21 that includes a flow meter 22 that measures the rate of flow of the sample leaving the cavity 11. The sample inlet tubing 20 has a first branching tubing 23 that is connected to the sample outlet tubing 21, which connection takes place through a three-way valve 24 disposed at an upstream point to the flow meter 22. A second branching tubing 26 branches off from the sample inlet tubing 20 through a three-way valve 26 and merges with the sample outlet tubing 19 through a three-way valve 27. A data processing black box 28 receives the signals from the light sensor 17 and the flow meter 22 and puts out the information on the mass concentration of a chemical elements dissolved or suspended in the sample, which information may be of a nature of the reading 29 of the normalized electric current originating from the light sensor as a function of time.

The preferred mode of operation of the accumulative absorption spectrophotometer 1 described in conjunction with FIG. 1 is as follows: Prior to every measurement of a sample, the filter 3 is back-washed by directing a sample flow from the sample inlet tubing 20 to the port 14 by turning the three-way valve 24 to "wash" position. The three-way valves 26 and 27 are also turned to "wash" position allowing the sample medium entering the apparatus through the port 14 to exit through the ports 12 and 13. The filter 3 may be further washed by directing the sample flow from the inlet tubing 20 to the ports 13 and 14, and by directing the sample flow leaving the apparatus through the port 12 to the outlet tubing 19. Upon completion of the aforementioned washing process, the three-way valves 24, 26 and 27 are turned to "measure" position, whereupon the sample medium enters the apparatus through the ports 12 and 13, flows across the tubular filter 3 and leaves the apparatus through the port 14. The movement of the chemical elements dissolved or suspended in the sample medium is blocked by the filter 3 and, consequently, the mass concentration of those elements starts to increase within the tubular filter 3 and a mass concentration boundary layer begins to form adjacent to the inside surface of the tubular filter. As more and more chemical elements accumulates within the tubular filter 3, greater amounts of the light passing through the through hole 4 is absorbed. The black box 28 detects the electric current of $I_o$ originating from the light sensor 28 at time $t_o$ when a washing cycle is completed and a measuring cycle begins. As the chemical elements retained in the mass concentration boundary layer within the tubular filter 3 increases, the electric current I originating from the light sensor 17 decreases until time $t_1$ when another washing cycle takes place, which lasts until time $t_2$ whereupon another measuring cycle takes place, as shown in data display 29. One combination of a washing cycle and a measuring cycle may have a period as short as a few seconds or a few minutes or as long as a few hours or a few days. The normalized electric current $I/I_o$ depends only on the amount of the chemical elements accumulating in the mass concentration boundary layer within the tubular filter, but it is independent of the physical and optical boundary conditions of the apparatus. In other words $$\frac{d}{dt}\left(\frac{I}{I_o}\right) = f(\dot{M}, C)$$

or $$C = g\left[\frac{d}{dt}\left(\frac{I}{I_o}\right), \dot{M}\right].$$

where M is the rate of mass flow measured by the flow meter 22 and C is the percent mass concentration of the chemical elements. The block box 28 analyzes the information on the time rate of change of the normalized electric current $[d/(dt)](I/I_o)$ and on the mass flow rate M and puts out the numerical value of the percent mass concentration of the chemical elements dissolved or suspended in the medium. In general, the period of each measuring cycle should be short enough so that the physical and optical boundary conditions in the measuring opparatus do not change during each measuring cycle due to the changes in the strength of the light source 15, in the sensitivity of the light sensor 17, in the transparency of the windows 7 and 8 and the lenses 16 and 18, etc. The analysis of the output data as well as the selection of the measuring period and its frequency may employ the principles of statics in order to further refine the accuracy and reliability of the output data from the accumulative absorption spectrophotometer 1 shown in FIG. 1. The inside diameter of the tubular filter 3 should be of the order of the thickness of the mass concentration boundary layer developing during each measuring period.

Figure 2:
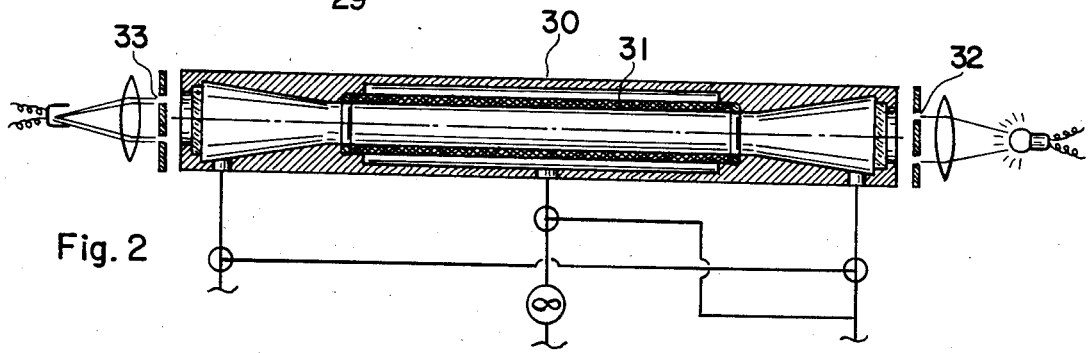
FIG. 2 illustrates a cross section of another embodiment of the accumulative absorption spectrophotometer of the present invention wherein a tubular filter of a large diameter is employed in creating a mass concentration boundary layer.

In FIG. 2 there is shown a cross section another accumulative absorption spectrophotometer 30 constructed and operating essentially in the same way as the apparatus shown in FIG. 1 with one exception being that the tubular filter 31 has a large diameter that is significantly greater than the thickness of the mass concentration boundary layer developing during each measuring period. An annular window 32 disposed in the passage of the light beam produces a light beam of a hollow cylindrical configuration that passes substantially through the mass concentration boundary layer adjacent to the inner surface of the tubular filter 31. Another annular window 33 may be disposed in front of the light sensing system.

Figure 3:
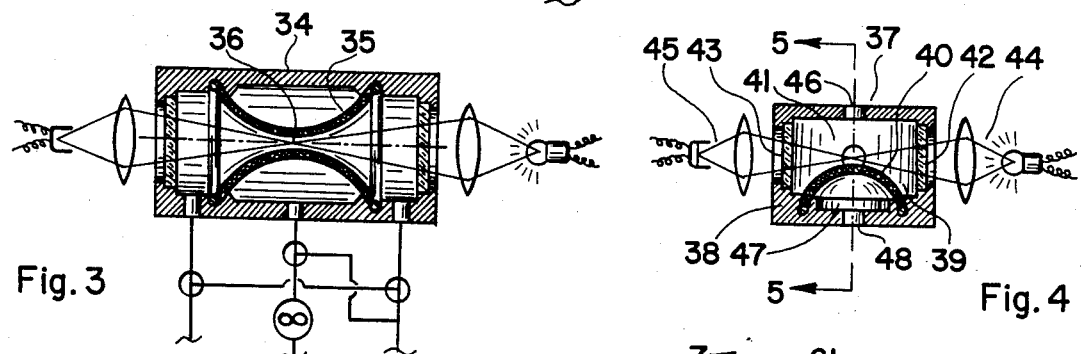
FIG. 3 illustrates a cross section of a further embodiment of the accumulative absorption spectrophotometer of the present invention wherein a tubular filter having a small throat opening is employed in creating a mass concentration boundary layer.

In FIG. 3 there is shown a cross section of a further accumulative absorption spectrophotometer that is constructed and operating essentially in the same principle as that shown in FIG. 1. The accumulative absorption spectrophotometer 34 employs a converging-diverging tubular filter 35 that has a small throat opening 36. The light beam coaxially passing through the interior of the tubular filter 35 is focused to the throat 36 of the converging-diverging tubular filter 35.

Figure 4:
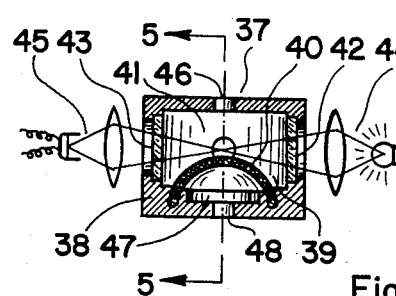
FIG. 4 illustrates a cross section of an accumulative absorption-dispersion spectrophotometer employing a convex disc filter in creating a mass concentration boundary layer.

In FIG. 4 there is shown a cross section of an embodiment of the accumulative absorption-dispersion spectrophotometer of the present invention which cross section is taken along a plane including the central axis of the apparatus. The accumulative absorption-dispersion spectrophotometer 37 comprises a cylindrical body 38 including a cylindrical cavity 39 that is divided into two compartments by a convex disc filter 40 coaxially disposed with respect to the cylindrical cavity 39. The cylindrical wall of the convex-side cylindrical cavity 41 includes a pair of windows 42 and 43 disposed at two diametrically opposite positions. The light beam originating from a light source system 44 is focused to a region immediately adjacent to the convex side center of the disc filter 40 and the intensity of the light beam exiting from the cylindrical cavity 39 is measured by a light sensing system. The convex-side compartment 41 includes a port 46 disposed through one end of the cylindrical body 38, while the concave-side compartment 47 has a port 48 disposed through the other end of the cylindrical body 38. The light sensor system 45 detects the amount of light passing through the mass boundary layer immediately adjacent to the convex-side center of the disc filter 40 where the light beam is focused at.

Figure 5:
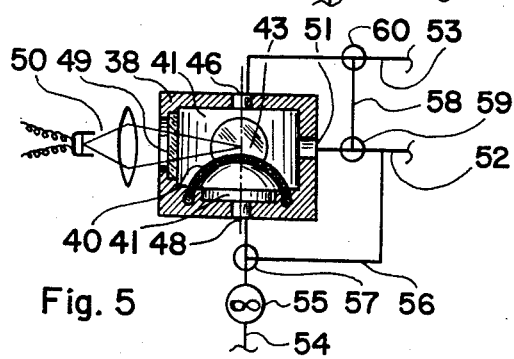
FIG. 5 illustrates another cross section of the accumulative absorption-dispersion spectrophotometer shown in FIG. 4 taken along a plane 5—5 as shown in FIG. 4.

In FIG. 5 there is shown another cross section of the accumulative absorption-dispersion spectrophotometer 37 of FIG. 4 taken along a plane 5—5 as shown in FIG. 4. The cylindrical wall of the convex-side compartment 41 including a third window 49 disposed intermediate two windows 42 and 43. There is a second light-sensing system 50 detecting the intensity of the scattered light originating from the mass concentration boundary layer immediately adjacent to the convex-side center of the disc filter 40 and exiting through the window 49. The light-sensing system 50 detecting the scattered light may be used to measure the turbidity of the medium caused by dissolved or suspended particles. An additional port 51 is disposed through the cylindrical wall of the convex-side compartment 41. The port 51 is connected to an inlet tubing 52, while the port 46 is connected to an outlet tubing 53. The port 48 is connected to another outlet tubing 54 including a flow meter 55. A first branching tubing 56 branching off from the inlet tubing 52 is connected to the outlet tubing 54 through a three-way valve 57 disposed at an upstream point to the flow meter 55. A second branching tubing 58 branching off from the inlet tubing 52 through a three-way valve 59 is connected to the outlet tubing 53 through a three-way valve 60. The procedure and method of washing and measuring with the accumulative absorption-dispersion spectrophotometer 37 are essentially the same as those described in conjunction with FIG. 1.

Figure 6:
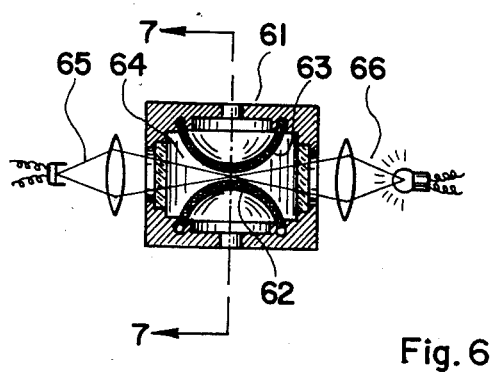
FIG. 6 illustrates a cross section of another accumulative absorption-dispersion spectrophotometer employing dual convex disc filters in creating a mass concentration boundary layer.

In FIG. 6 there is illustrated a cross section of another accumulative absorption-dispersion spectrophotometer 61 that is constructed and operated in a way similar to that shown in FIGS. 4 and 5. The apparatus 61 includes a pair of convex disc filters 62 and 63 coaxially disposed with respect to the center line of the cylindrical cavity 64 in a convex-side to convex-side arrangement. As a matter of face, two halves of this apparatus 61 divided by a plane including the center line of the light beam and perpendicular to the center line of the cylindrical cavity 64, are mirror images to each other and each half is exactly the same as one half of the apparatus 37 of FIG. 4 divided by a plane including the center line of the light beam and perpendicular to the central axis of the apparatus, which side includes the convex disc filter. The light-sensing system detects the intensity of the light beam passing through the mass concentration boundary layer occupying the narrowest gap between two convex-side filters 62 and 63 where the light beam originates from the light source system 66.

Figure 7:
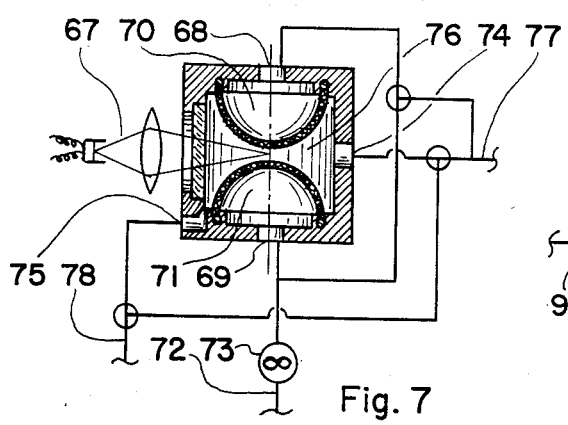
FIG. 7 illustrates another cross section of the accumulative absorption-dispersion spectrophotometer shown in FIG. 6 taken along a plane 7—7 as shown in FIG. 6.

In FIG. 7 there is illustrated another cross section of the apparatus 61 shown in FIG. 6 taken along a plane 7—7 as shown in FIG. 6. This cross section shows essentially the same elements as those appearing in the cross section shown in FIG. 5 which includes an additional light sensing system 67 detecting the intensity of the scattered light. The ports 68 and 69 open to the concave-side compartments 70 and 71 are connected to an outlet tubing 72 including a flow meter 73. Two ports 74 and 75 disposed through the cylindrical wall of the convex-side compartment 76, which are located at two diametrically opposite sides, are respectively connected to an inlet tubing 77 and an outlet tubing 78. The inlet and outlet tubings are connected to each other by the branching tubings and the three-way valves in the same way as those described in conjunction with FIG. 5. The accumulative absorption-dispersion spectrophotometer 61 shown in FIGS. 6 and 7 operates in the same way as that described in conjunction with FIG. 1.

Figure 8:
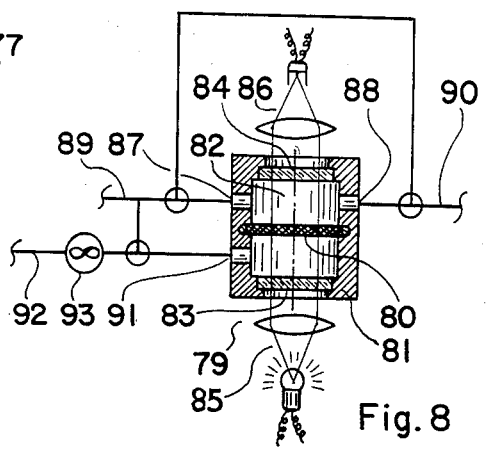
FIG. 8 illustrates an accumulative absorption spectrophotometer employing a light-transparent filter in creating a mass concentration boundary layer.

In FIG. 8 there is shown a cross section of an accumulative absorption spectrophotometer 79 employing a transparent disc filter 80, which cross section is taken along a plane including the center line of the apparatus. The cylindrical body 81 includes a cylindrical cavity 81 that is divided into two compartments by the transparent disc filter 80. The end walls of two compartments include the light-transparent windows 83 and 84. A light beam originating from a light source system 85 travels through the cylindrical chamber 82 in the direction parallel to the central axis of the cylindrical chamber 82 as it passes through the window 83, the transparent filter 80 and the window 84. The intensity of the light beam emerging through the window 84 is detected by a light-sensing system 86. One of two compartments constituting the cylindrical cavity 82 has two ports 87 and 88 disposed through the cylindrical wall thereof, which are located at two diametrically opposite positions. The port 87 is connected to an inlet tubing 89, while the port 88 is connected to an outlet tubing 90. The other of the two compartments constituting the cylindrical cavity 82 has a port 91 through the cylindrical wall thereof, which is connected to an outlet tubing 92 including a flow meter 93. The inlet tubing and the outlet tubings are inter-connected by the branching tubings and the three-way valves in the same manner as those described in conjunction FIG. 5. The accumulative absorption spectrophotometer 79 of FIG. 1 operates in the same principles as those described in conjunction with FIG. 1.

Figure 9:
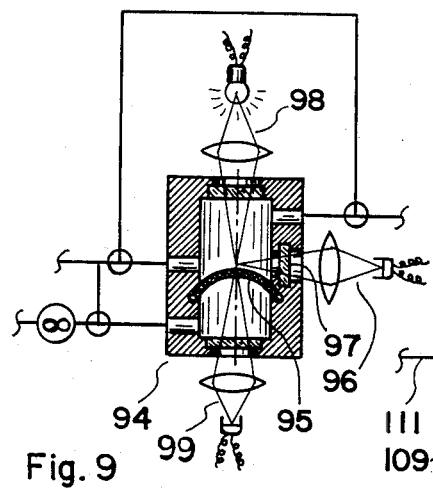
FIG. 9 illustrates an accumulative absorption-dispersion spectrophotometer employing a light-transparent convex filter in creating a mass concentration boundary layer.

In FIG. 9 there is shown a cross section of an accumulative absorption-dispersion spectrophotometer 94 that is constructed essentially in the same way as the apparatus 79 of FIG. 8 with a few exceptions being that the apparatus 94 employs a transparent convex-disc filter and includes a second light-sensing system 96 that senses the scattered light that originates from the mass concentration boundary layer immediately adjacent to the convex-side center of the transparent convex disc filter 95, which dispersed light emerges through a window 97 disposed through the cylindrical wall of the convex-side compartment. The light beam originating from the light source system 98 is focused to the mass concentration boundary layer immediately adjacent to the convex-side center of the transparent convex disc filter 95. The light-sensing system 99 senses the intensity of the light transmitted through the mass concentration boundary layer. It should be understood that the sample under measurement has to be introduced into the convex-side compartment and taken out from the convex-side compartment during measuring cycle. The operating principles of the apparatus 94 are the same as those described in conjunction with FIG. 1.

Figure 10:
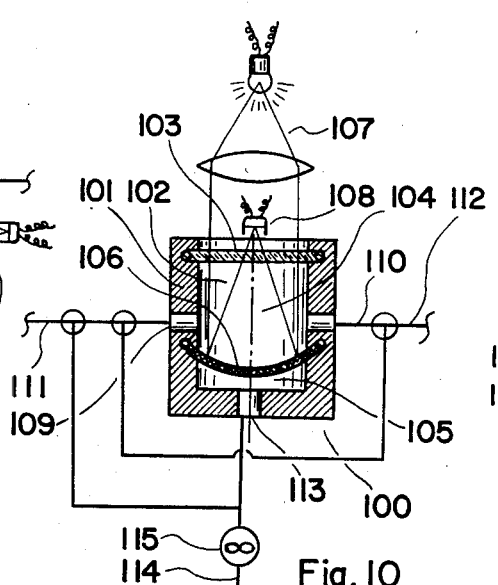
FIG. 10 illustrates an accumulative absorption spectrophotometer employing a light-reflecting parabolic disc filter in creating a mass concentration boundary layer.

In FIG. 10 there is illustrated a cross section of an embodiment of the accumulative absorption spectrophotometer constructed in accordance with the principles of the present invention that employs a light-reflecting parabolic disc filter, which cross section is taken along a plane including the central axis of the apparatus. The accumulative absorption spectrophotometer 100 comprises a body 101 including a cylindrical cavity 102 with one open end that is sealed off with a transparent window 103. The cylindrical cavity 102 is divided into two compartments 104 and 105 by a parabolic disc filter 106 having its concave side surface lined with a light-reflecting surface, wherein the concave side thereof faces the window 103. A parallel light beam emitted from a light source system 107 disposed exteriorly to the cylindrical cavity 102 enters the compartment 104 through the window 103 and is reflected back to a focal point located outside of the window 103 by the parabolic mirror filter 106. A light sensing system 108 located at the focal point detects the intensity of the reflected light that twice crosses the mass concentration boundary layer adjacent to the reflecting surface of the parabolic mirror. The concave-side compartment 104 includes a pair of the ports 109 and 110 respectively connected to an inlet tubing 111 and an outlet tubing 112. The convex-side compartment 105 includes a port 113 that is connected to an outlet tubing 114 including a flow meter 115. The inlet tubing and the outlet tubings are inter-connected by the branching tubings and three-way valves in the same way as the arrangement described in conjunction with FIG. 5. The operating principles and procedures of the accumulative absorption spectrophotometer 100 shown in FIG. 10 are the same as those described in conjunction with FIG. 1.

Figure 11:
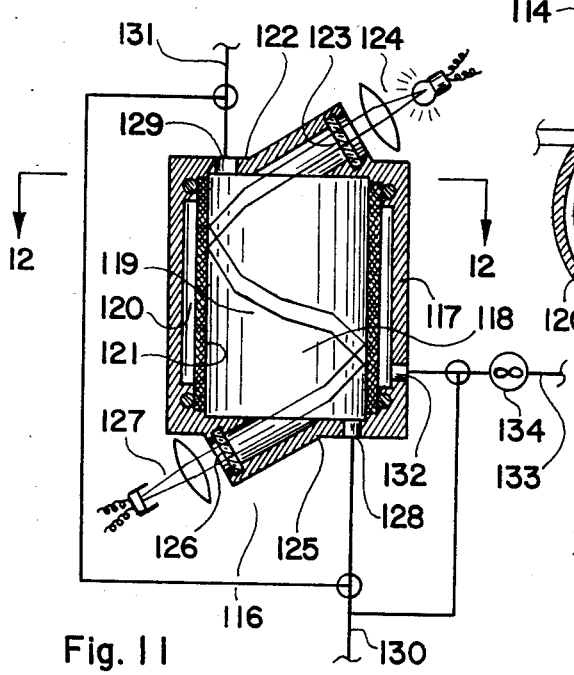
FIG. 11 illustrates an accumulative absorption spectrophotometer employing a light-reflecting tubular filter of a large diameter in creating a mass concentration boundary layer.

In FIG. 11 there is illustrated a cross section of an embodiment of the accumulative absorption spectrophotometer employing a light reflecting tubular filter, which cross section is taken along a plane including the central axis of the apparatus. The accumulative absorption spectrophotometer 116 comprises a body 117 including a cylindrical cavity 118 disposed therein, which is divided into an inner compartment 119 and an outer compartment 120 by a tubular filter 121 having its inner cylindrical surface coated with a light reflecting lining. The tubular filter 121 is disposed in a coaxial relationship within the cylindrical cavity 118. One end wall 122 of the cylindrical cavity 118 includes a window 123 disposed adjacent to the light reflecting cylindrical surface of the tubular filter 121 through which a light beam originating from a light source system 124 enters the cylindrical cavity 118 in a direction substantially tangential to the cylindrical wall of the tubular filter 121 and in a shallow oblique angle with respect to a plane perpendicular to the central axis of the apparatus. The other end wall 125 of the cylindrical cavity 118 includes a window 126 through which the light beam entering through the window 123 exits after traveling a substantially helical path through the mass concentration boundary layer adjacent to the inside surface of the tubular filter 121. The window 126 is disposed in such a way that the light beam leaving the cylindrical cavity 118 in a direction substantially tangential to the cylindrical wall of the tubular filter 121 and in a shallow oblique angle with respect to a plane perpendicular to the central axis of the apparatus, passes through the window 126 and lands on a light sensing system 127. The inner compartment 119 includes a pair of ports 128 and 129 respectively connected to an inlet tubing 130 and an outlet tubing 131. The outer annular cylindrical compartment 120 has a port 132 connected to an outlet tubing 133 that includes a flow meter 134. The operating principles and procedures of the accumulative absorption spectrophotometer 116 are the same as those described in conjunction with FIG. 1.

Figure 12:
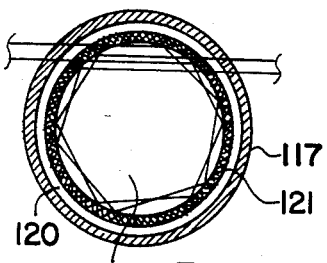
FIG. 12 illustrates another cross section of the accumulative absorption spectrophotometer shown in FIG. 11 taken along a plane 12—12 as shown in FIG. 11.

In FIG. 12 there is illustrated another cross section of the accumulative absorption spectrophotometer 116 of FIG. 11 taken along a plane 12—12 as shown in FIG. 12. The light beam entering the cylindrical cavity 118 through the window 123 in a direction substantially tangential to the cylindrical wall of the tubular filter 121 is repeatedly reflected by the light reflecting inner surface of the tubular filter 121 and travels through the mass concentration boundary adjacent to the inner surface of the tubular filter 121 following a substantially helical path until it exits through the window 126.

Figure 13:
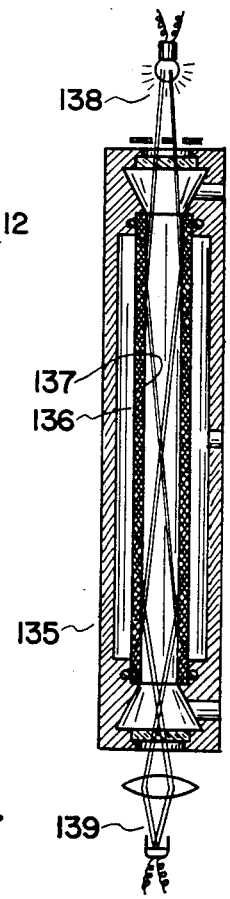
FIG. 13 illustrates another accumulative absorption spectrophotometer employing a light-reflecting tubular filter of a small diameter in creating a mass concentration boundary layer.

In FIG. 13 there is illustrated a cross section of an embodiment of the accumulative absorption spectrophotometer of the present invention employing a tubular filter with a light reflecting inner cylindrical surface, which cross section is taken along a plane including the central axis of the apparatus. The accumulative absorption spectrophotometer 135 is constructed essentially in the same way as the apparatus 30 shown in FIG. 2 with two exceptions being that the tubular filter 136 has its inner cylindrical surface 137 coated with a light-reflecting lining, and that the light beam originating from the light source system is of a hollow conical pattern. The light beam of a hollow conical pattern becomes repeatedly reflected by the light-reflecting inner cylindrical surface 137 of the tubular filter 136 and follows a series of diverging-converging hollow conical pattern. The light beam exiting the inner compartment within the tubular filter after repeatedly passing through the mass concentration boundary layer adjacent to the inner cylindrical surface of the tubular filter, is measured by the light sensing system 139. The operating principles and procedures of the accumulative absorption spectrophotometer 135 are the same as that described in conjunction with FIG. 1.

Figure 14:
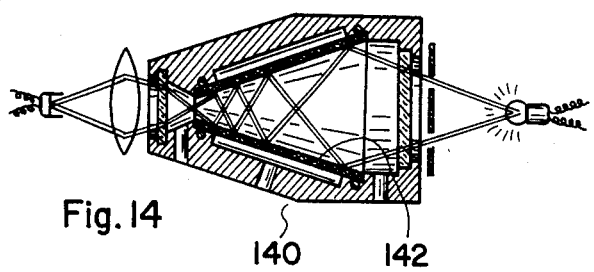
FIG. 14 illustrates a further accumulative absorption spectrophotometer employing a light-reflecting conical frustum shell filter in creating a mass concentration boundary layer.

In FIG. 14 there is illustrated a cross section of another accumulative absorption spectrophotometer 140 constructed and operated in essentially the same principles as that of FIG. 13. The accumulative absorption spectrometer 140 employs a hollow conical frustum filter or tapered tubular conical filter 141 instead of a tubular filter of a constant diameter. The cone angle of the tapered tubular filter 142 should be shallow enough so that the light beam introduced thereinto through the larger open end becomes funneled therethrough and exits through the smaller open end. It should be understood that embodiments shown in FIGS. 1, 2, 3, 4 and 6 may also employ filters with a light-reflecting surface, even though there is no well defined advantage arising from the use of the light-reflecting filter in those embodiments.

While the principles of the present invention have now been made clear by the illustrative embodiments, it will be immediately obvious to those skilled in the art many modifications of the arrangements, elements, proportions, structures and materials, which are particularly adapted to the specific working environments and operating conditions in the practice of the invention without departing from those principles.

I claim:

1. A device for measuring the concentration of chemical substances dissolved or suspended in a medium comprising in combination:
    (a) a cell for holding said medium with dissolved or suspended substances, wall of said cell including at least in part a filter blocking the movement of said substances while allowing the movement of said medium thereacross, said cell including window arrangement allowing a beam of a radiant energy to enter said cell, pass by said filter in a close proximity and leave said cell;
    (b) a source of said beam of a radiant energy disposed exteriorly to said cell;
    (c) a sensor receiving and measuring the intensity of said beam of a radiant energy leaving said cell after passing through a mass concentration boundary layer formed adjacent to said filter, said sensor disposed exteriorly to said cell;
    (d) means for continuously supplying said medium to said cell and for continuously removing said medium leaving said cell through said filter wherein said filter creates said mass concentration boundary layer adjacent to said cell-side surface of said filter during a measuring period;
    (e) means for washing off said mass concentration boundary layer adjacent to said cell-side surface of said filter during a washing period; and
    (f) means for measuring the amount of flow of said medium across said filter; wherein said sensor measures the increase of the concentration of said substances in said mass concentration boundary layer during a measuring period following a washing period and said means for measuring the amount of flow measures the flow of said medium causing said increase of the concentration of said substances in said mass concentration boundary layer; whereby, the concentration of said substances in said medium is obtained.

2. The combination as set forth in claim 1 wherein said source of said beam of a radiant energy includes means for producing a beam of monochromatic or a narrow bands of a radiant energy.

3. The combination as set forth in claim 1 wherein said combination includes another sensor receiving and measuring the intensity or flux of scattered radiant energy orginating from said beam of a radiant energy passing through said mass concentration boundary layer adjacent to said cell-side surface of said filter; whereby the turbidity of said medium is obtained.

4. A device for measuring the turbidity of a medium including dissolved or suspended substances, said device comprising in combination:
    (a) a cell for holding said medium with dissolved or suspended substances, wall of said cell including at least in part a filter blocking the movement of said substances while allowing the movement of said medium thereacross, said cell including window arrangement allowing a beam of a radiant energy to enter said cell and pass by said filter in a close proximity;
    (b) a source of said beam of a radiant energy disposed exteriorly to said cell;
    (c) a sensor receiving and measuring the intensity or flux of scattered radiant energy orginating from said beam of a radiant energy passing through a mass concentration boundary layer formed adjacent to said filter, said sensor disposed exteriorly to said cell;
    (d) means for continuously supplying said medium to said cell and for continuously removing said medium leaving said cell through said filter wherein said filter creates said mass concentration boundary layer adjacent to said cell-side surface of said filter during a measuring period;
    (e) means for washing off said mass concentration boundary layer adjacent to said cell-side surface of said filter during a washing period; and
    (f) means for measuring the amount of flow of said medium across said filter;
wherein said sensor measures the increase of the concentration of said substances in said mass concentration boundary layer during a measuring period following washing period and said means for measuring the amount of flow measures the flow of said medium causing said increase of the concentration of said substances in said mass concentration boundary layer; whereby, the turbidity of said medium is obtained.

5. A device for measuring the concentration of chemical substances dissolved or suspended in a medium comprising in combination:
    (a) a cell for holding said medium with dissolved or suspended substances wherein said cell is divided into two compartments by a transparent filter blocking the movement of said substances while allowing the movement of said medium thereacross, said cell including window arrangement allowing a beam of a radiant energy to enter said cell, pass through said transparent filter and leave said cell;
(b) a source of said beam of a radiant energy disposed exteriorly to said cell;
(c) a sensor receiving and measuring the intensity or flux of said beam of a radiant energy leaving said cell after passing across a mass concentration boundary layer formed adjacent to said transparent filter, said sensor disposed exteriorly to said cell;
(d) means for continuously supplying said medium to one of said two compartments included in said cell and for continuously removing said medium from the other of said two compartments included in said cell wherein said transparent filter creates said mass concentration boundary layer adjacent to said transparent filter during a measuring period;
(e) means for washing off said mass concentration boundary layer adjacent to said transparent filter during a washing period; and
(f) means for measuring the amount of flow of said medium across said transparent filter;
wherein said sensor measures the increase of the concentration of said substances in said mass concentration boundary layer during a measuring period following a washing period and said means for measuring the amount of flow of said medium measures the flow of said medium causing said increase of the concentration of said substances in said mass concentration boundary layer; whereby, the concentration of said substances is obtained.

6. The combination as set forth in claim 5 wherein said source of said beam of a radiant energy includes means for producing a beam of monochromatic or a narrow bands of a radiant energy.

7. The combination as set forth in claim 5 wherein said combination includes another sensor receiving and measuring the intensity or flux of scattered radiant energy orginating from said beam of a radiant energy passing across said mass concentration boundary layer adjacent to said transparent filter; whereby, the turbidity of said medium is obtained.

8. A device for measuring the concentration of chemical substances dissolved or suspended in a medium comprising in combination:
(a) a cell for holding said medium with dissolved or suspended substances, wall of said cell including at least in part a filter with a radiant energy reflecting surface, said filter blocking the movement of said substances while allowing the movement of said medium thereacross, said cell including window arrangement allowing a beam of a radiant energy to enter said cell, impinge on and reflected by said filter, and leave said cell;
(b) a source of said beam of a radiant energy disposed exteriorly to said cell;
(c) a sensor receiving and measuring the intensity or flux of said beam of a radiant energy leaving said cell after repeatedly passing across a mass concentration boundary layer formed adjacent to said cell-side reflecting surface of said filter;
(d) means for continuously supplying said medium to said cell and for continuously removing said medium leaving said cell through said filter wherein said filter creates said mass concentration boundary layer adjacent to said cell-side reflecting surface of said filter during a measuring period;
(e) means for washing off said mass concentration boundary layer adjacent to said cell-side reflecting surface of said filter during a washing period; and
(f) means for measuring the amount of flow of said medium across said filter;
wherein said sensor measures the increase of the concentration of said substances in said mass concentration boundary layer during a measuring period following a washing period and said means for measuring the amount of flow measures the flow of said medium causing said increase of the concentration of said substances in said mass concentration boundary layer; whereby, the concentration of said substances in said medium is obtained.

9. The combination as set forth in claim 8 wherein said source of said beam of a radiant energy includes means for producing a beam of monochromatic or a narrow bands of a radiant energy.

10. The combination as set forth in claim 8 wherein said combination includes another sensor receiving and measuring the intensity or flux of scattered radiant energy originating from said beam of a radiant energy passing through said mass concentration boundary layer adjacent to said cell-side reflecting surface of said filter; whereby, the turbidity of said medium is obtained.

11. The combination as set forth in claim 8 wherein said cell-side reflecting surface of said filter comprises a parabolic surface with a focal point substantially coinciding with said sensor.

* * * * *